United States Patent
Rossger et al.

(10) Patent No.: US 10,415,054 B2
(45) Date of Patent: Sep. 17, 2019

(54) DESIGNER CIRCUIT CONTROLLING DIET-INDUCED OBESITY

(71) Applicant: ETH ZURICH, Zurich (CH)

(72) Inventors: Katrin Rossger, Zurich (CH); Martin Fussenegger, Magenwil (CH)

(73) Assignee: ETH ZURICH, Zurich (SE)

( * ) Notice: Subject to any disclaimer, the term of this patent is extended or adjusted under 35 U.S.C. 154(b) by 57 days.

(21) Appl. No.: 14/765,665

(22) PCT Filed: Feb. 3, 2014

(86) PCT No.: PCT/EP2014/000268
§ 371 (c)(1),
(2) Date: Aug. 4, 2015

(87) PCT Pub. No.: WO2014/117945
PCT Pub. Date: Aug. 7, 2014

(65) Prior Publication Data
US 2015/0368666 A1 Dec. 24, 2015

(30) Foreign Application Priority Data

Feb. 4, 2013 (EP) .................................... 13000564

(51) Int. Cl.
| | | |
|---|---|---|
| C12N 15/85 | (2006.01) | |
| A61K 35/12 | (2015.01) | |
| C12N 15/09 | (2006.01) | |
| A61K 38/10 | (2006.01) | |
| A61K 38/18 | (2006.01) | |
| A61K 38/22 | (2006.01) | |
| A61K 38/26 | (2006.01) | |
| A61K 38/27 | (2006.01) | |
| A61K 9/00 | (2006.01) | |
| A61K 9/50 | (2006.01) | |
| A61K 47/69 | (2017.01) | |

(52) U.S. Cl.
CPC ............ *C12N 15/85* (2013.01); *A61K 9/0024* (2013.01); *A61K 9/5036* (2013.01); *A61K 35/12* (2013.01); *A61K 38/10* (2013.01); *A61K 38/105* (2013.01); *A61K 38/1825* (2013.01); *A61K 38/1866* (2013.01); *A61K 38/22* (2013.01); *A61K 38/2207* (2013.01); *A61K 38/2264* (2013.01); *A61K 38/26* (2013.01); *A61K 38/27* (2013.01); *A61K 47/6901* (2017.08); *C12N 15/09* (2013.01); *A01K 2207/12* (2013.01); *A01K 2227/105* (2013.01); *A01K 2267/0393* (2013.01); *C12N 2800/107* (2013.01); *C12N 2800/60* (2013.01); *C12N 2830/002* (2013.01)

(58) Field of Classification Search
None
See application file for complete search history.

(56) References Cited

U.S. PATENT DOCUMENTS

| | | | | |
|---|---|---|---|---|
| 2006/0160088 A1* | 7/2006 | Golz | ...................... | G01N 33/92 |
| | | | | 435/6.16 |
| 2007/0036770 A1* | 2/2007 | Wagner | .............. | A61K 48/0008 |
| | | | | 424/93.21 |
| 2011/0178112 A1* | 7/2011 | Kristiansen | .......... | A61K 31/357 |
| | | | | 514/278 |

FOREIGN PATENT DOCUMENTS

| | | | |
|---|---|---|---|
| WO | WO 2000/078986 | * | 12/2000 |
| WO | WO 2004/019869 | | 3/2004 |
| WO | WO 2010/115583 | * | 10/2010 |

OTHER PUBLICATIONS

Gurnell et al., J. Biol. Chem. 2000, 275(8)5754-5759.*
Machine Translation (Google) of WO 2000/078986 referenced above, translation completed on Mar. 27, 2017.*
Teayoun et al., "Generation of an inducible, cardiomyocyte-specific transgenic mouse model with PPAR beta/delta overexpression," Methods Mol. Biol. 952:57-65 (2013).
Kong et al., "Display of aggregation-prone ligand binding domain of human PPAR gamma on surface of bacteriophage lambda" Acta Pharmacologica Sinica 27:91-9 (2006).
Weber et al. "A biotin-triggered genetic switch in mammalian cells and mice," Metab. Eng. 11:117-24 (2009).
Velkov et al., "Ligand-enhanced expression and in-cell assay of human peroxisome proliferator-activated receptor alpha ligand binding domain," Prot Exp Purif 70:260-9 (2010).
Goto et al., "Natural compounds regulate energy metabolism by the modulating the activity of lipid-sensing nuclear receptors," Moi. Nutr. Food Res. 57:20-33 (2013).
Rössger et al. "A closed-loop synthetic gene circuit for the treatment of diet-induced obesity in mice," Nat. Commun. 4:2825 (2013).
International Search Report dated Aug. 13, 2014 in International Application No. PCT/EP2014/000268.
Written Opinion of the International Searching Authority dated Aug. 13. 2014 in related International Application No. PCT/EP2014/000268.
International Preliminaly Report on Patentability dated Aug. 4, 2015 in related International Application No. PCT/EP2014/000268.

* cited by examiner

Primary Examiner — James D Schultz
(74) Attorney, Agent, or Firm — Medler Ferro Woodhouse & Mills PLLC

(57) ABSTRACT

The invention relates to vectors and mammalian cells in a system useful for switching on or switching off gene expression in response to fatty acids, and a method of treating diet-induced obesity. In particular, a synthetic intracellular lipid-sensing receptor was constructed that constantly monitors blood fatty acid levels, processes diet-associated hyperlipidemia and coordinates reversible and adjustable expression of the anorectic peptide hormone pramlintide to reduce dietary intake, blood fat levels and body weight.

8 Claims, 9 Drawing Sheets

Specification includes a Sequence Listing.

DESIGNER CIRCUIT CONTROLLING DIET-INDUCED OBESITY

FIELD OF THE INVENTION

The invention relates to vectors and mammalian cells in a system useful for switching on or switching off gene expression in response to fatty acids, and a method of treating diet-induced obesity.

BACKGROUND OF THE INVENTION

Diet-induced obesity typically results from a combination of excessive food energy intake, favored by an evolutionary remain associating energy-dense food with greater taste, lack of physical activity and genetic susceptibility. Obesity is at the origin of a wide range of diseases such as cardiovascular disorders, type 2 diabetes, obstructive sleep apnea, osteoarthritis, asthma and certain types of cancer and has become a leading preventable cause of death with dramatically increasing prevalence, affecting up to 1.5 billion people in industrialized and developing countries. A sustainable change in lifestyle including dieting and physical exercise is the pillar for the treatment of obesity that can be complemented by gastric balloon and bariatric surgery to assist weight loss and by taking anti-obesity drugs to reduce appetite or fat absorption. However, dieting often shows limited success, surgery is associated with significant risks, and only some anti-obesity drugs with modest efficacy remain on the market after many have been withdrawn because of side effects and few have entered clinical trials since. The amylin analogue pramlintide has recently been licensed as injection-based adjunctive type 2 diabetes therapy as it reduces adsorption of glucose and other nutrients such as fat by slowing gastric emptying, promotes satiety via GLP-1-independent hypothalamic receptors and inhibits inappropriate secretion of glucagon (Younk, L. M. et al., *Expert Opin Pharmacother* 12, 1439-1451 (2011)). However, precise injection-based dosing at mealtime remains challenging due the short half-life of the synthetic peptide hormone.

Synthetic biology-inspired designer networks that coordinate caloric intake to satiety responses could control dietary energy homeostasis and may provide a new strategy for the treatment of obesity.

SUMMARY OF THE INVENTION

The invention relates to a mammalian cell comprising (a) a lipid-sensing receptor comprising the human peroxisome proliferator-activated receptor alpha (PPARα) or a related receptor fused to an activator or repressor, linked to a minimal promoter to control transgene expression, and (b) a polynucleotide coding for an endogenous or exogenous protein reducing fat intake or being easily detectable.

Likewise, the invention relates to a vector comprising a lipid-sensing receptor comprising the human peroxisome proliferator-activated receptor alpha (PPARα) or a related receptor fused to an activator or repressor, linked to a minimal promoter to control transgene expression.

In particular the invention relates to such a mammalian cell and to such vector comprising a fusion protein of PPARα or the related receptor with a phloretin-responsive repressor (TtgR) that binds a TtgR-specific operator ($O_{TtgR}$) linked to the minimal promoter.

Furthermore the invention relates to the mentioned mammalian cell in a nano- or microcontainer, a mammal excluding man comprising such a mammalian cell optionally in a nano- or microcontainer, and to a method of treating diet-induced obesity administering such vectors and/or cells.

(b) Interaction of fatty acids (FA) with a receptor leads to its activation, starts a signaling cascade to turn the inactive protein kinase to an active one either directly or via G-proteins (G) and second messenger (sm), which are formed from pro-second messengers (Pro-sm) by the adenylyl cyclase (AC), further releases the PK catalytic subunit (C) to activate a response element (RE), and hence initiates transgene (TG) expression by binding to the response element-specific promoter ($P_{RE}$).

(c) Molecular configuration of OFF-type and ON-type mammalian gene regulation systems. In the OFF-type system, a bacterial DNA-binding protein (DBP), fused to a mammalian transactivation domain (TA) binds to a specific operator module and induces polymerase (Poly)-mediated transcription of the transgene (TG) from a minimal promoter ($P_{min}$). DBP-TA only binds to its cognitive operator in the absence of fatty acids (FA). In the ON-type system, the DBP is fused to a mammalian transcription repressor domain (TR), binds to the specific operator sequence located downstream of a constitutive promoter, and thus represses its transcription. Upon addition of fatty acids (FA), repression is abolished and transgene (TG) expression takes place.

Figure 2:
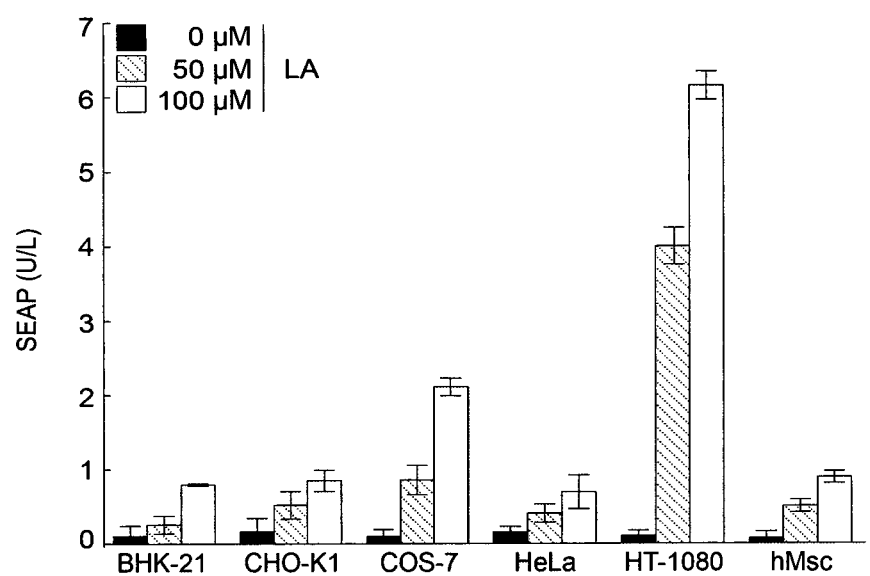

FIG. 2: Versatile applicability of the LSR devise

Linoleic acid-induced SEAP expression in different cell lines. Cells were cotransfected with the LSR-encoding expression vector (pKR135; $P_{hCMV}$-LSR-pA) and the $P_{TtgR1}$-driven SEAP expression plasmid (pMG10; $P_{hCMV*-1}$-SEAP-pA), grown in the presence of different linoleic acid (LA) concentrations, and SEAP levels were profiled in the culture supernatant after 48 h.

Figure 3:
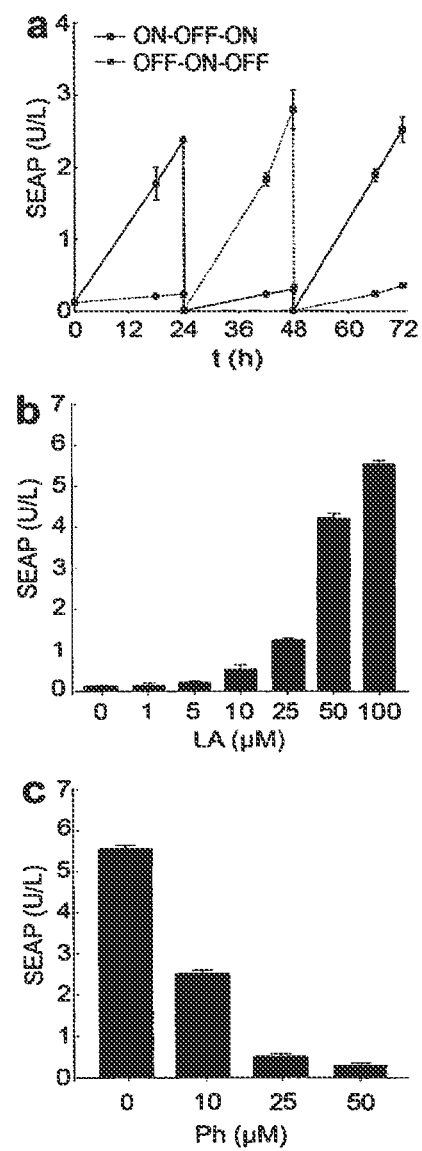
Figure 3:
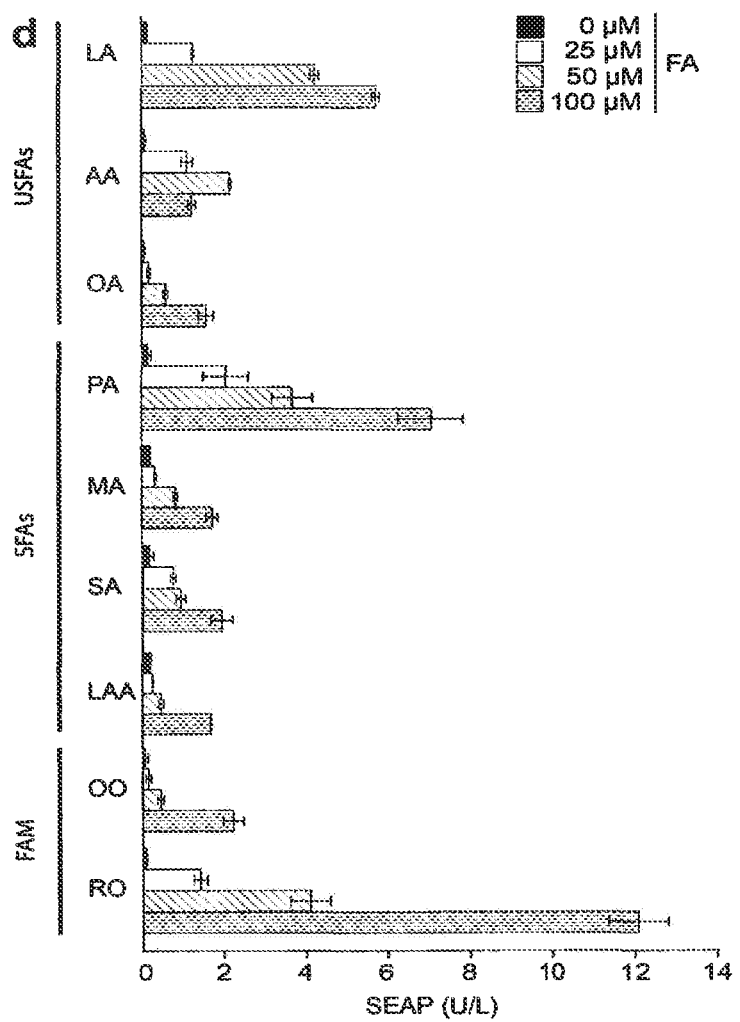
Figure 3:
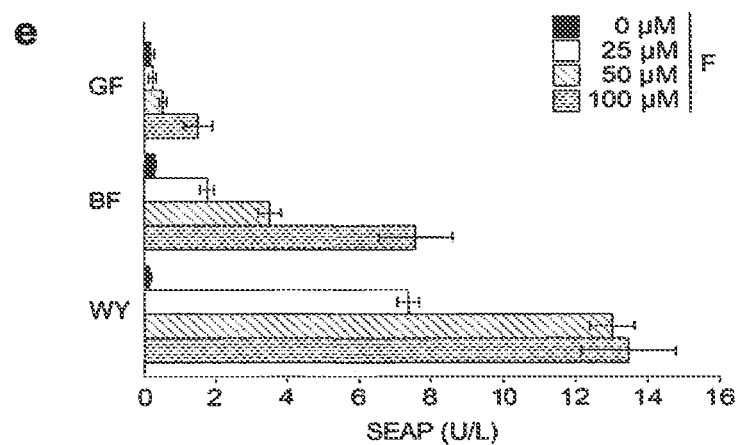

FIG. 3: Characterization of fatty acid-controlled transgene expression (a) Reversibility of fatty acid-responsive SEAP expression was assessed by cultivating transgenic HT-1080 (pKR135/pMG10) for 72 h while alternating the linoleic acid status of the culture (100 μM ON, 0 μM, OFF) at 24 h and 48 h.

—■—ON-OFF-ON; ••••■•••• OFF-ON-OFF.

(b) Adjustability of fatty-acid inducible SEAP expression. pKR135-/pMG10-transgenic HT-1080 were cultivated in medium containing increasing linoleic acid (LA) concentrations and corresponding SEAP production was quantified in the culture supernatant after 48 h.

(c) Phloretin-triggered safety switch. pKR135-/pMG10-engineered HT-1080 were programmed for maximum expression by 100 µM linoleic acid followed by addition of different concentrations of phloretin (Ph) before SEAP expression was scored after 48 h.

(d) Sensitivity of the LSR control switch to different fatty acids. HT-1080 containing the LSR device were exposed for 48 h to different concentrations of specific fatty acids before SEAP expression was assessed. USFAs=unsaturated fatty acids (LA=linoleic acid, AA=arachidonic acid, OA=oleic acid); SFAs=saturated fatty acids (PA=palmitic acid, MA=myristic acid, SA=staeric acid, LAA=lauric acid); FAM=fatty acid mixture (OO=olive oil, RO=rapeseed oil).

(e) Tunability of the LSR control device in response to clinically licensed fibrate drugs. LSR-transgenic HT-1080 (pKR135/pMG10) were cultivated in the presence of different concentrations of fibrate drugs (F) and SEAP production was profiled after 48 h. GF=gemfibrozil, BF=bezafibrate, WY=WY-14643.

Figure 4:
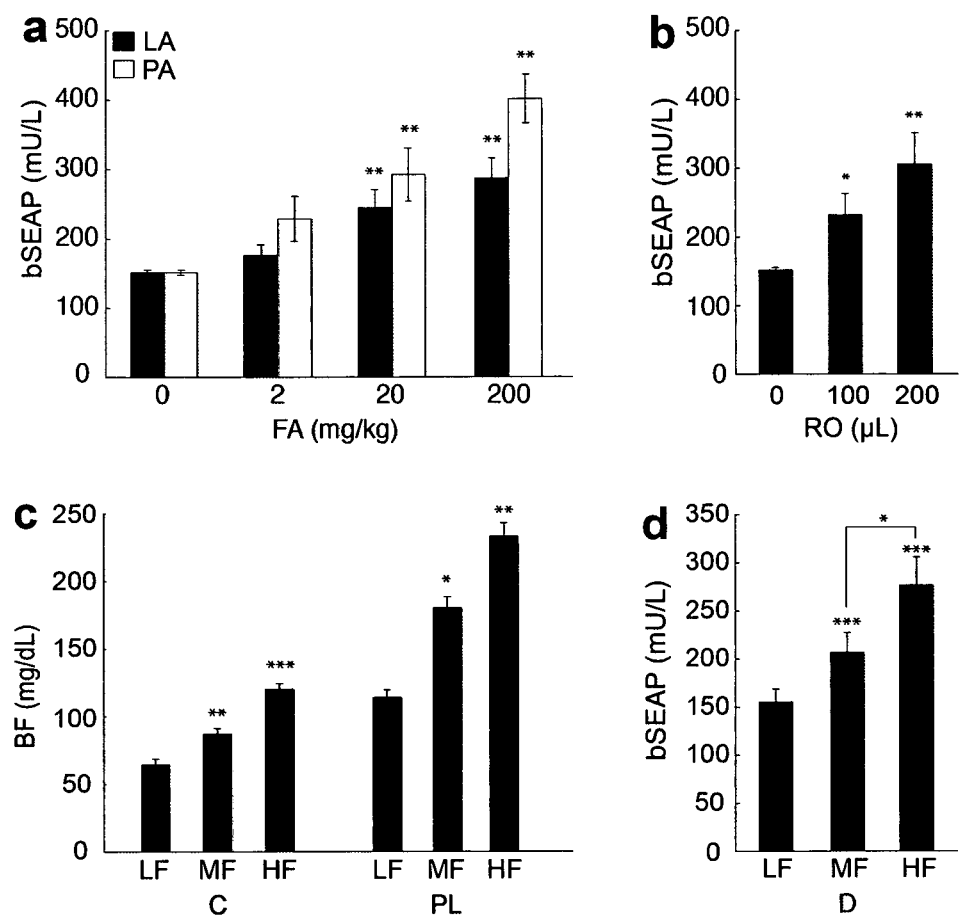

FIG. 4: Performance of fatty acid-inducible expression control in wild type mice (a-d) Standard low fat-fed wild type mice were implanted with microencapsulated pKR135-/pMG10-transgenic HT-1080 ($2\times10^6$ cells/mouse) and received different doses of linoleic acid (LA) and palmitic acid (PA) (fatty acids, FA) (a), rapeseed oil (RO) (b) or were put on standard low fat (LF, 5 kcal % fat), medium fat (MF, 10 kcal % fat) and high fat (HF, 60 kcal % fat) diets (D) (c, d). Resulting blood SEAP (bSEAP) levels (a, b, d) and blood fat levels (BF) represented by serum cholesterol (C) and phospholipid (PL) concentrations (c) were quantified after 48 h (a, b, d) or 72 h (c). Data are mean±SEM, statistics by two-tailed t test; n=8 mice. *P<0.05, P<0.005, *P<0.0001 vs. zero lipid doses (a,b) or LF mice (c,d).

Figure 5:
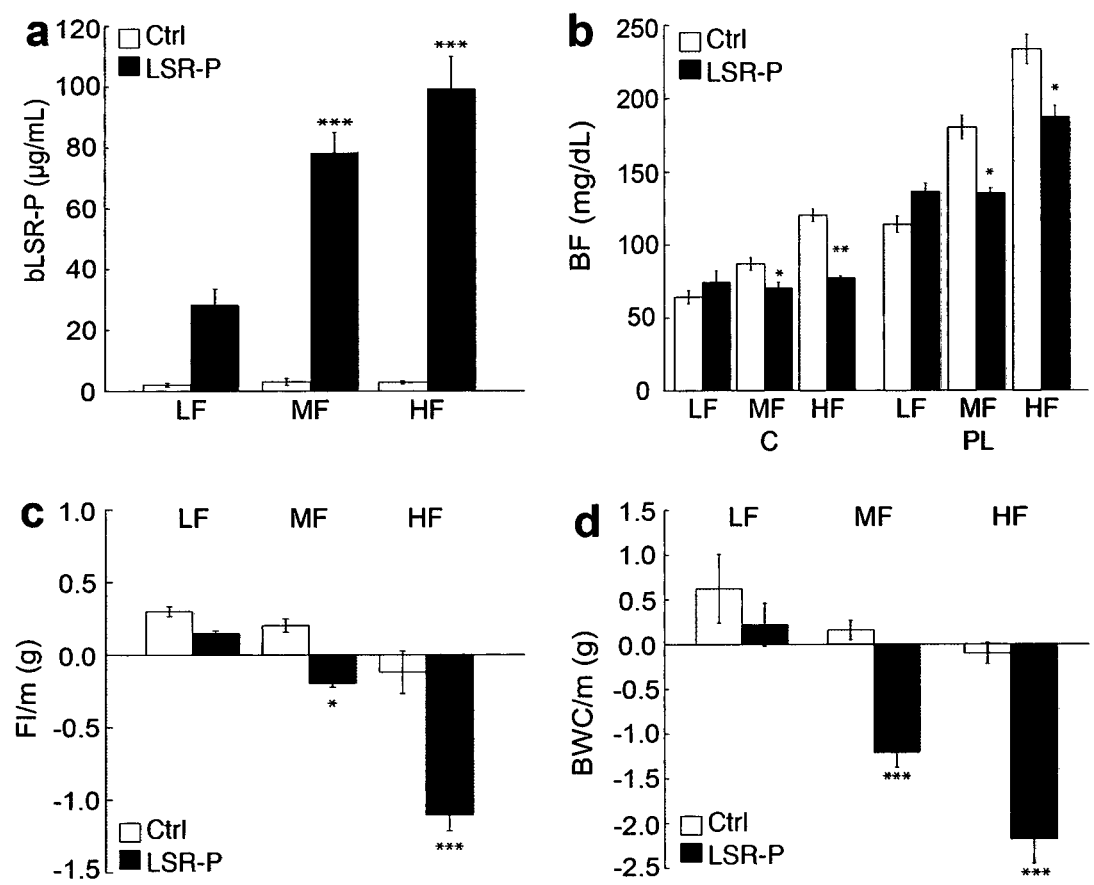

FIG. 5: Self-sufficient LSR-based control of pramlintide expression in diet-induced obese mice.

(a-d) Mice fed for 14 weeks with standard low fat (LF, 5 kcal % fat), medium fat (MF, 10 kcal % fat) and high fat (HF, 60 kcal % fat) diets were implanted with pKR135/pKR146-transgenic HT-1080 ($2\times10^6$ cells/mouse) (LSR-Pramlintide, LSR-P) or the isogenic pKR135/pMG10-transgenic HT-1080 ($2\times10^6$ cells/mouse) (Control, Ctrl). 72 h after implantation, blood LSR-pramlintide levels (bLSR-P) (a) and blood fat levels (BF) represented by serum cholesterol (C) and phospholipid (PL) concentrations (b), as well as food intake per mouse (FI/m) (c), and weight loss (body weight change per mouse, BWC/m) (d) were profiled. Data are mean±SEM, statistics by two-tailed t test; n=8 mice. *P<0.05, P<0.005, *P<0.0001 vs. LF mice.

Figure 6:
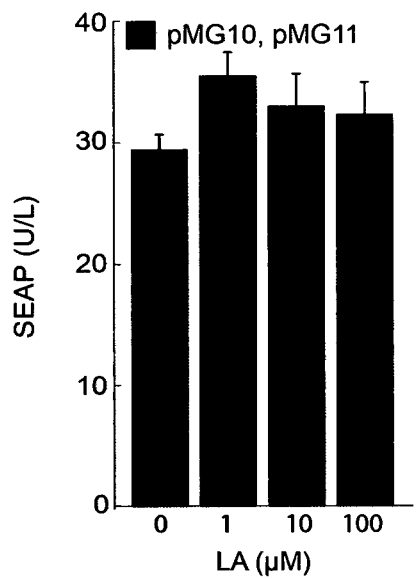

FIG. 6: Insensitivity of the phloretin-responsive control element to linoleic acid HT-1080 were cotransfected with the components encoding the phloretin-responsive gene switch (pMG10, ($P_{TtgR1}$-SEAP-pA) and pMG11, ($P_{SV40}$-TtgA$_1$-pA)) and grown for 48 h in the presence of increasing linoleic acid (LA) concentrations before SEAP was profiled in the cell culture supernatant.

Figure 7:
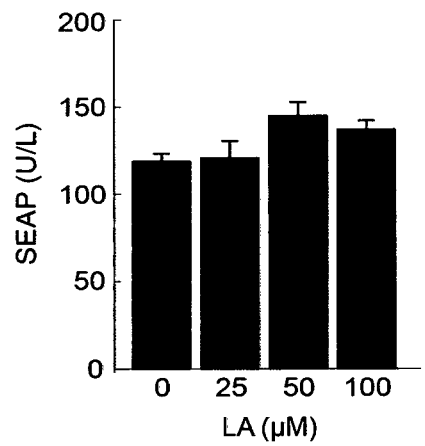

FIG. 7: Viability of HT-1080 exposed to increasing concentrations of Linoleic acid HT-1080 were transfected with pSEAP2-control ($P_{SV40}$-SEAP-pA) and exposed to increasing concentrations of linoleic acid (LA). Any negative impact of excessive fatty acid on the metabolism or viability of the cells would impair their overall SEAP production capacity.

Figure 1:
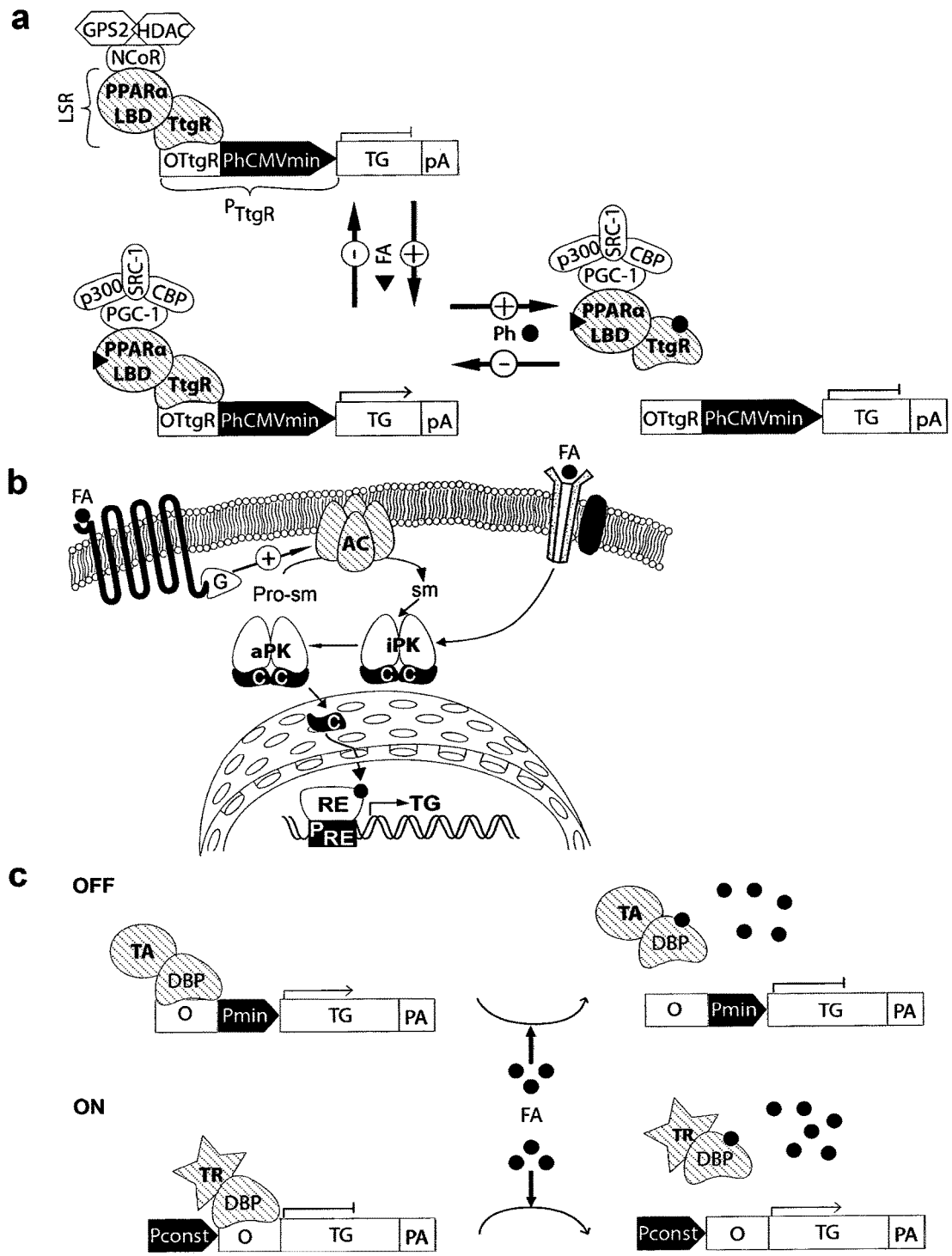
FIG. 1: Synthetic fatty acid-responsive mammalian sensor-based gene switch (a) The synthetic lipid-controlled mammalian transcription device consists of an intracellular lipid-sensing receptor (LSR), a fusion protein combining the phloretin-responsive repressor (TtgR) and the human peroxisome proliferator-activated receptor alpha (PPARα), that binds a TtgR-specific operator ($O_{TtgR}$) linked to a minimal promoter ($P_{hCMVmin}$) ($P_{TtgR1}$) to control transgene expression. In the absence of fatty acids (FA), LSR associates with an inhibitory complex (GPS2, G-protein pathway suppressor 2; HDAC, histone deacetylase; NCoR, nuclear receptor corepressor) to repress transgene (TG) expression, which switches to full induction in the presence of fatty acids when LSR associates with the activation complex (SRC1, steroid receptor coactivator 1; p300, E1A binding protein; CBP, CREB-binding protein; PGC-1, peroxisome proliferator-activated receptor-γ coactivator). Transgene expression can also be shut down by disrupting LSR-promoter binding by addition of the clinically licensed skin-penetrating apple metabolite phloretin (Ph).
Figure 8:
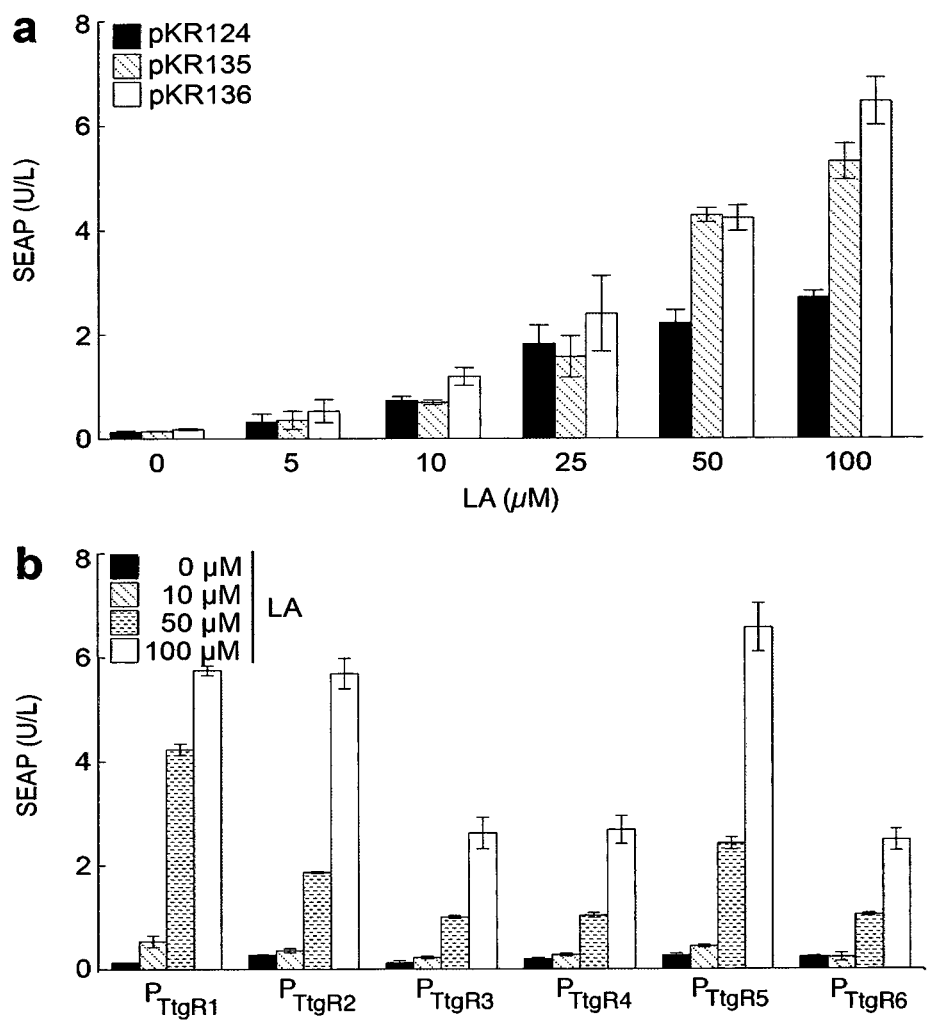

FIG. 8: Optimization of LSR's fatty acid sensitivity (a) HT-1080 were (co-)transfected with pMG10 ($P_{TtgR1}$-SEAP-pA) and an expression vector encoding LSR under control of different constitutive promoters (pKR124, $P_{SV40}$-LSR-pA; pKR135, $P_{hCMV}$-LSR-pA; pKR136, $P_{hEF1\square}$-LSR-pA) and cultivated in the presence of increasing concentrations of linoleic acid (LA) for 48 h before SEAP was profiled in the culture supernatant. (b) HT-1080 were (co-)transfected with the LSR expression vector pKR135 ($P_{hCMV}$-LSR-pA) and reporter constructs encoding SEAP under control of different LSR-specific promoter variants containing 0 ($P_{TtgR1}$; pMG10), 2 ($P_{TtgR2}$; pMG20), 4 ($P_{TtgR3}$; pMG21), 6 ($P_{TtgR4}$; pMG22), 8 ($P_{TtgR5}$; pMG23) and 10 ($P_{TtgR6}$; pMG24) base pair linkers between the TtgR operator ($O_{TtgR}$) and the minimal promoter ($P_{hCMVmin}$) (see FIG. 1). Transfected HT-1080 were cultivated in the presence of different linoleic acid (LA) concentrations and SEAP expression was profiled after 48 h.

Figure 9:
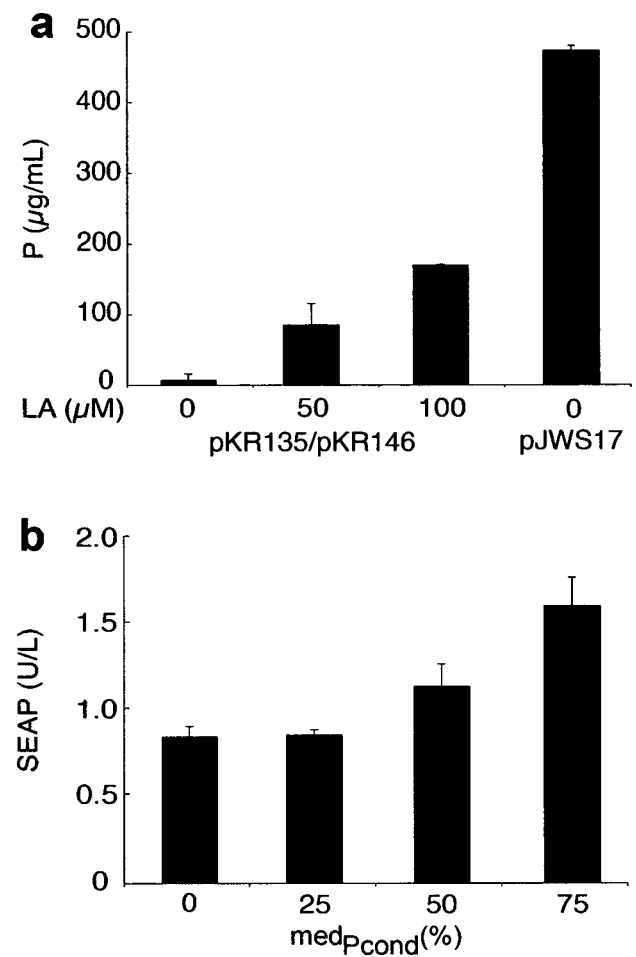

FIG. 9: Characterization of pramlintide expression (a) Comparative analysis of linoleic acid (LA)-induced LSR-driven (pKR135/pKR146) and constitutive (pJWS17, $P_{hCMV}$-Pram-pA) pramlintide (P) expression by HT-1080 (co-) transfected with indicated vectors and cultivated for 48 h.

(b) Validation of functional pramlintide production. The culture supernatant of pKR135/pKR146-transgenic pramlintide-producing HT-1080 cultivated for 48 h in the presence of 100 µM linoleic acid was mixed at different percentages with DMEM and used to cultivate HEK-293 (co-)transfected with expression vectors encoding the pramlintide-specific receptors pCALCR, pRAMP3 and the corresponding reporter unit (pCK53; $P_{CRE}$-SEAP-pA). Pramlintide-triggered SEAP expression was profiled after 48 h. med$_{Pcond}$ (%)=pramlintide-containing conditioned medium, % pramlintide.

DETAILED DESCRIPTION OF THE INVENTION

The invention relates to a mammalian cell comprising (a) a lipid-sensing receptor comprising the human peroxisome proliferator-activated receptor alpha (PPARα) or a related receptor fused to an activator or repressor, linked to a minimal promoter to control transgene expression, and (b) a polynucleotide coding for an endogenous or exogenous protein reducing fat intake or being easily detectable.

Furthermore the invention relates to such mammalian cell wherein the human peroxisome proliferator-activated receptor alpha (PPARα) or a related receptor fused to an activator or repressor is a fusion protein of PPARα or the related protein with a phloretin-responsive repressor (TtgR) that binds a TtgR-specific operator ($O_{TtgR}$) linked to the minimal promoter.

Likewise, the invention relates to a vector comprising a lipid-sensing receptor comprising the human peroxisome proliferator-activated receptor alpha (PPARα) or a related receptor fused to an activator or repressor, linked to a minimal promoter to control transgene expression, in particular a vector comprising a fusion protein of PPARα or the related receptor with a phloretin-responsive repressor (TtgR) that binds a TtgR-specific operator ($O_{TtgR}$) linked to the minimal promoter.

A lipid-sensing receptor is, for the purpose of the invention, a protein, which detects and quantifies lipids in free and bound form. In particular the lipid-sensing receptor is a fusion protein, which binds different lipophilic molecules such as saturated lipids, for example propionic acid, lauric acid, myristic acid, palmitic acid, stearic acid, arachidic acid, and in particular all lipid numbers C3:0-C36:0, or unsaturated lipids, for example myristoleic acid, palmitoleic acid, sapienic acid, oleic acid, elaidic acid, vaccenic acid, linoleic acid, linoelaidic acid, α-linoleic acid, arachidonic acid, eicosapentaenoic acid, erucic acid, and docosahexaenoic acid, or also sphingolipids, phospholipids, lipoproteins, lipid hormones and lipid hormone derivatives, sterols, and cholesterol and cholesterol derivatives, and thereby modulates transcription.

A "related receptor" is a receptor which is, for example, derived from the mentioned receptor human peroxisome proliferator-activated receptor alpha (PPARα). By "derived from" a receptor, is meant, in this context, that the amino acid sequence is almost identical to the amino acid sequence of the natural receptor, contains only conservative amino substitutions and remains at least 70%, preferably 80%, and more preferably 90% identical at the amino acid level. By "related to" a natural receptor PPARα is meant, for purposes of the invention, that the polynucleotide sequence that encodes the amino acid sequence hybridizes to a naturally occurring polynucleotide sequence encoding PPARα under at least low stringency conditions, more preferably moderate stringency conditions, and most preferably high stringency conditions, and retains the pH sensing properties. Conservative substitution is known in the art and described by Dayhof, M. D., 1978, Nat. Biomed. Res. Found., Washington, D.C., Vol. 5, Sup. 3, among others. Genetically encoded amino acids are generally divided into four groups: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. Phenylalanine, tryptophan and tyrosine are also jointly classified as aromatic amino acids. A substitution of one amino acid in a particular group with another amino acid in the same group is generally regarded as a conservative substitution. It is understood, for the purpose of this invention, that "derived from" and "related to" also includes compounds at the polynucleotide level comprising triplet codons coding for the same amino acid but being especially adapted to the intended host cell, e.g. mammalian cell. Such polynucleotides especially adapted to mammalian cells are particularly preferred.

A "related" receptor according to the invention is also a PPARβ, PPARγ, Cyp7A1, FXR, or LXR receptor, or a PPARα receptor or the mentioned related receptors derived from a non-human animal, for example from mouse or rat.

Furthermore, a "related" receptor according to the invention is also a signalling pathway activating receptor such as CD36, TLR4 and 6, GRP40, 41, 43, 119, 120, or the mentioned related receptors derived from a non-human animal, for example from mouse or rat, that initiates transgene expression through direct or indirect (G-Protein, second messenger) activation of the inactive protein kinase, which thereby induces transcription factors to bind to its response element-specific promoters.

Additionally, a "related" receptor of this invention is also the transcription factor CmeR, KstR, or BreR, which activates transgene expression by binding or release from its cognitive operator.

In place of the phloretin-responsive repressor (TtgR) that binds a TtgR-specific operator ($O_{TtgR}$), other repressors or activators may be used. Accordingly the TtgR-specific operator sequence ($O_{TtgR}$) may be replaced by the AlcR-specific operator sequence ($O_{AlcA}$), the ArgR-specific operator sequence ($O_{ARG}$), the ETR operator element, the EthR-specific operator module ($O_{EthR}$), the HdnoR-specific operator sequence ($O_{Nic}$), the PIP operator element, the ScbR-specific operator module ($O_{ScbR}$), hucO, VanO, TetO, or the TrpR-specific operator sequence ($O_{TrpR}$) recognized by AlcR, ArgR, MphR, EthR, HdnoR, Pip, ScbR, HucR, VanR, TetR or TrpR, respectively, when fused to PPARα.

Additionally, the phloretin-responsive repressor (TtgR) can be replaced by artificial transcription factors containing designer zinc-finger DNA-binding domains, which activate or repress gene expression (Pollock, R. et al., Nat biotechnol 20 (7), 729-733 (2002)) or by site specific DNA-binding proteins called transcription activator-like effector (TALE) proteins, that can be readily designed to target new sequences (Zhang, F. et al., Nat biotechnol 29 (2), 149-153 (2011)).

Furthermore, the invention relates to a mammalian expression vector comprising a polynucleotide for a protein reducing fat intake. Such proteins are, for example, amylin, leptin, adiponectin, pramlintide, GLP-1, PYY, uroguanylin, nesfatin, human growth hormone fragment AOD9604, fibroblast growth factor 19 and 21, VEGF-B, bombesin, and cholecystokinin. In particular the protein reducing fat intake is amylin and analogues of amylin, for example pramlintide. Especially such a mammalian expression vector is a vector comprising a $P_{TtgR1}$-driven unit.

The invention further relates to a mammalian cell as defined above in a nanocontainer or microcontainer, e.g. in encapsulated form to protect the cells from environmental stress while providing best conditions of living. A nanocontainer may be a virus, preferably an attenuated virus, in particular a viral capsid, synthetic or semi-synthetic nano- or microparticles, such as spheres or tubes of a suitable geometry to incorporate mammalian cells, and the nano- or microcontainers formed in situ by encapsulation of mammalian cells, for example with alginate-poly-L-lysine. A particular example of a suitable nano- or microcontainer is the polysulfone hollow fiber manufactured under the trade name CELLMAX®. Further preferred materials for nano- or microcontainer are cellulose sulfate (CS) poly-diallyldimethyl ammonium chloride, starch and starch derivatives, dextran and chitosan.

The invention further relates to a mammal excluding man comprising a mammalian cell as described, in particular a mammalian cell in a nano- or microcontainer.

Furthermore the invention relates to a treatment of obesity, comprising administering to a patient in need thereof an effective amount of a mammalian cell according to the invention, preferably in encapsulated form.

A transactivation (TA) domain is, for example, the vp16 transactivation domain of Herpes simplex virus, the p65 transactivation domain, the human e2f4 transactivation domain, and transactivation domains derived from or related to GAL4, CTF/NF1, AP2, ITF1, Oct1 and SpI, and also those listed in U.S. Pat. No. 6,287,813.

A transrepressor (TR) domain is, for example, the krab transrepression domain of human Kruppel-associated box-protein. Other transrepressor domains considered are domains derived from or related to, for example, the v-erbA oncogenes product, the thyroid hormone receptor, steroid hormone receptors, the Ssn6/Tup1 protein complex, the SIRI protein, NeP1, TSF3, SF1, WT1, Oct-2.1, E4BP4, ZF5, PPARα, PPARβ, PPARγ, LXR, FXR, RXR, YY1, any transcriptional regulator containing a PhD bromo domain and also those listed in U.S. Pat. No. 6,287,813.

A promoter considered is, for example, the constitutive simian virus 40 promoter ($P_{SV40}$), the minimal human cytomegalovirus immediate early promoter ($P_{hCMVmin}$), the constitutive human cytomegalovirus promoter ($P_{hCmv}$), the human elongation factor 1α promoter ($P_{hEF1\alpha}$), the phosphoglycerate kinase promoter ($P_{PGK}$), the human ubiquitin promoter ($P_{hUBc}$), the activator protein-1 promoter ($P_{AP1}$), the cAMP response element promoter ($P_{CRE}$), the nuclear factor of activated T-cells promoter ($P_{NFAT}$), the nuclear factor 'kappa-light-chain-enhancer' of activated B-cells promoter ($P_{NF\kappa B}$), and the beta-actin promoter.

A protein easily detectable is, for example, human placental secreted alkaline phosphatase (SEAP), a fluorescent or enhanced fluorescent protein (e.g. GFP, RFP, YFP, and the like), secreted alpha amylase (SAMY), luciferase, beta-galactosidase, beta-lactamase, and glucoronidase.

The ligand-binding domain of PPARα was fused to the bacterial repressor TtgR (WO 2010/115583 A1) to create a synthetic transcription factor, the lipid-sensing receptor (LSR), that retains dual-input sensitivity to fatty acids as well as to the transdermal control compound phloretin and specifically activates chimeric promoters ($P_{TtgR1}$) in an adjustable manner.

In humans, peroxisome proliferator-activated receptor alpha (PPARα) is a nuclear lipid receptor heterodimerizing with the retinoic X receptor (RXR) to form a transcription factor that constitutively binds to specific target promoters (Kumar, R. & Thompson, E. B., *Steroids* 64, 310-319 (1999)). Through interaction with regulatory co-activators such as the steroid receptor coactivator 1 (SRC1), the peroxisome proliferator-activated receptor-γ coactivator 1 (PGC-1), the CREB-binding protein (CBP) and the E1A binding protein p300 or with specific co-repressors like the nuclear receptor corepressor (NCoR), the G-protein pathway suppressor 2 (GPS2) and the histone deacetylase (HDAC) PPARα manages uptake, utilization and catabolism of fatty acids in a variety of tissues such as liver, kidney, heart, muscle and adipose. PPARα's activity is modulated by binding of fatty acids (e.g., linoleic acid, a plant-derived fatty acid and palmitic acid, an animal-derived fatty acid) (Krey, G. et al., *Mol Endocrinol* 11, 779-791 (1997)) and synthetic fibrate drugs licensed for the treatment of hyperlipidemia (Kersten, S. et al., *Nature* 405, 421-424 (2000)).

The ligand-binding domain of PPARα was fused to the bacterial repressor TtgR (WO 2010/115583 A1) to create a synthetic transcription factor, the lipid-sensing receptor (LSR), that retains dual-input sensitivity to fatty acids as well as to the transdermal control compound phloretin and specifically activates chimeric promoters ($P_{TtgR1}$) in an adjustable manner (FIG. 1a). Cotransfection of several rodent, primate and human cell lines with the constitutive LSR expression vector pKR135 ($P_{hCMV}$-LSR-pA; LSR, TtgR-PPARα) and the LSR-dependent SEAP reporter construct pMG10 ($P_{TtgR1}$-SEAP-pA) showed that SEAP was exclusively induced whenever the cells were exposed to exogenous linoleic acid (FIG. 2). Since the isogenic transcription factor TtgA$_1$ (pMG11, TtgR-VP16) was insensitive to fatty acids in an identical experimental set-up, LSR's lipid-sensing capacity indeed resides in its PPARα domain while the TtgR moiety mediates sequence-specific binding (FIG. 6). Differences in the cellular portfolio of promiscuous PPARα-coregulatory components and lipid metabolism may in part explain the differences in basal expression and induction profiles among different cell lines. Control experiments showed that neither ectopic expression of LSR nor exposure of the cells to excessive fatty acid concentrations had a negative impact on their viability (FIG. 7). Further experiments using different constitutive promoters to drive LSR and different LSR-specific target promoters confirmed that the combination of pKR135, pMG10 and HT-1080 cells showed the best fatty acid-triggered transgene induction and was therefore used in all follow-up experiments (FIG. 8). Detailed characterization of pKR135/pMG10-transgenic HT-1080 cells revealed that the synthetic fatty acid sensor circuit was fully reversible (FIG. 3a) and precisely adjusted transgene expression levels in response to a wide range of fatty acid concentrations (FIG. 3b). At the same time LSR retained its dose-dependent sensitivity to the licensed cosmetic additive phloretin that could release LSR from $P_{TtgR1}$, override fatty acid induced transcription control and shut down transgene expression (FIG. 3c).

LSR is sensitive to a broad spectrum of fatty acids including unsaturated (linoleic acid, arachidonic acid, oleic acid) and saturated (palmitic acid, myristic acid, stearic acid, lauric acid) ones of plant (linoleic acid) and animal (palmitic acid, stearic acid, myristic acid) origin as well as to complex fatty acids mixtures such as dietary oils (FIG. 3d). For example, while linoleic and palmitic acids mediated up to 55-fold induction of SEAP expression, rapeseed oil reached induction factors of up to 140 (FIG. 3d). LSR is also sensitive to fibrates such as WY-14643, gemfibrozil (LOPID®) and bezafibrate (BEZALIP®) (FIG. 3e), a class of synthetic amphipathic carboxylic acids that are clinically licensed for the treatment of hyperlipidemia. The LSR controller device can also be used for drug-controlled expression of therapeutic transgenes and combined with fibrate-based therapies.

Covering a wide range of dietary and synthetic fatty acids at high sensitivity, the LSR-based sensor device has all it takes to precisely score physiologic fatty levels. To validate fatty acid-triggered product gene expression in vivo, pKR135/pMG10-transgenic HT-1080 variants engineered for fatty acid-controlled SEAP expression were microencapsulated in coherent alginate-poly-alginate beads (Weber, W. et al., *Nat Biotechnol* 20, 901-907 (2002)) and intraperitoneally implanted into wild type mice kept on a standard diet. The animals were treated with diverse concentrations of linoleic and palmitic acid or received different oral doses of rapeseed oil while control mice obtained an identical fatty acid-free care. Mice with LSR implants that were treated with lipid supplements showed a significant dose-dependent increase of SEAP in their serum (FIG. 4a,b). This proves that the LSR sensor device is able to monitor, process and report hyperlipidemia in vivo while the circuit remains shut down at physiologic blood fat levels reached during a standard diet. To confirm the in vivo precision of the LSR sensor device, microencapsulated pKR135/pMG10-transgenic HT-1080 cells was also implanted into diet-induced obese mice put on medium-fat (MF; 10 kcal % fat) as well as high-fat (HF; 60 kcal % fat) diets, and their blood fatty acid and SEAP levels compared to non-obese control animals with a standard caloric low-fat intake (LF; 5 kcal % fat) (FIG. 4c,d). LSR-transgenic cell implants are able to indirectly score the food quality by sensing specific blood fat levels represented by serum cholesterol and phospholipids (FIG. 4c) and produce the corresponding SEAP expression response that results in serum SEAP levels specific for each diet group (FIG. 4d).

In order to automatically control diet-induced obesity in a self-sufficient manner the LSR sensor device was functionally coupled to expression of the clinically licensed anorectic peptide hormone pramlintide (Khan, A. et al.; *Recent Pat Endocr Metab Immune Drug Discov* 6, 117-128 (2012)), which promotes satiety and slows gastric emptying, thereby limiting high-caloric food intake, attenuating hyperlipidemic blood levels, reducing body weight and restoring the energy homeostasis of the organism. SEAP in pMG10 was replaced by pramlintide and the resulting vector pK146 (P$_{TtgR1}$-Pram-pA) validated for LSR-controlled pramlintide production using ELISA (FIG. 9a) as well as a cell-based assay confirming pramlintide's capacity to activate its target CALC/RAMP receptor and trigger the corresponding signaling cascades (FIG. 9b). To test the designer circuit's capacity to control diet-induced obesity pKR135/pKR146-engineered HT-1080 was implanted into diet-induced obese mice receiving high-fat (HF; 60 kcal % fat) or medium-fat (MF; 10 kcal % fat) diets as well as wild type mice receiving standard food (LF; 5 kcal % fat), and pramlintide levels, blood fat concentrations, food intake and body weight profiled for several days (FIG. 5). While treated diet-induced obese mice showed a significant diet-dependent increase in circulating pramlintide levels (FIG. 5a) leading to reduction of food consumption (FIG. 5b), blood fat levels (FIG. 5c) and body weight (FIG. 5d), all of these values remained unchanged in animals receiving standard food (FIG. 5a-d). It is of particular importance that standard-fed wild type mice implanted with the LSR-driven pramlintide device kept their body weight proving that the designer network is only active in an obesity risk situation involving excess fat and stops pramlintide production to prevent underfeeding (FIG. 5a,d).

Synthetic biology-inspired control devices and gene networks that precisely reprogram the dynamic behavior, metabolism and physiology of mammalian cells have reached a level of sophistication which enables the community to rapidly move forward and start to shape new clinical applications and treatment concepts. Therapeutic networks combining sensor and effector devices that, upon integration into cells and functional connection to their metabolism, monitor disease-relevant metabolites, process on/off level control and coordinate adjusted therapeutic responses that restore metabolite homeostasis in a seamless, automatic and self-sufficient manner are particularly attractive for future gene and cell-based therapies. The LSR-pramlintide circuit represents a prototype for such a therapeutic designer circuit. The LSR sensor captures a wide range of lipids within their physiologic concentration range, becomes dose-dependently activated by peak fatty acid levels and shuts down at native concentrations. In combination with the pramlintide-encoding effector component and implanted into diet-induced obese mice the designer circuit (i) constantly monitored blood fatty acid levels, (ii) processed peak fat values, (iii) produced a coordinated pramlintide production response that (iv) reduced food intake, (v) decreased blood fat levels, (vi) dropped the body weight, and (vii) automatically switched off at normal blood fat levels. Also, since the LSR used TtgR as DNA-binding component the designer device can be switched off at any time using a skin lotion containing the clinically licensed apple metabolite phloretin, which may represents an additional safety latch in future clinical applications. With obesity being on its way to develop into a global epidemic, available pharmacotherapies showing limited success and an almost dried-out drug pipeline synthetic biology-based gene- and cell-based therapies foster new opportunities in the treatment of obesity and related diseases.

Experimental Procedures

Lipid Sensor Components

Comprehensive design and construction details for all expression vectors are provided in the following Table 1:

| Plasmid | Description and Cloning Strategy | Reference or Source |
|---|---|---|
| pcDNA3.1 | Mammalian expression vector (P$_{hCMV}$-MCS-pA). | Life Technologies, Carlsbad, CA, USA |
| pSEAP2-control | Constitutive mammalian SEAP expression vector (P$_{SV40}$-SEAP-pA). | Clontech, Mountain View, CA, USA |
| pCALCR | Constitutive pcDNA3.1-derived CALCR expression vector (P$_{hCMV}$-CALCR-pA). | www.cdna.org |
| pRAMP3 | Constitutive pcDNA3.1-derived RAMP3 expression vector (P$_{hCMV}$-RAMP3-pA). | www.cdna.org |
| pUC57-Pram | Custom-designed pUC57-derived vector containing pramlintide. | GenScript Inc. Piscataway, NJ, USA |
| pCK53 | Vector encoding a P$_{CRE}$-driven SEAP expression unit (P$_{CRE}$-SEAP-pA). | Kemmer C. et al., Journal of Controlled Release 150, 23 (2011) |
| pMG10 | Vector encoding a P$_{TtgR1}$-driven SEAP expression unit (P$_{TtgR1}$-SEAP-pA). | WO2010115583A1 |
| pMG11 | Constitutive mammalian TtgA$_1$ expression vector (P$_{SV40}$-TtgA$_1$pA; TtgA$_1$, TtgR-VP16). | WO2010115583A1 |
| pWW29 | Constitutive mammalian MphR(A) expression vector (P$_{hEF1\alpha}$-MphR(A)-pA). | Weber W. et al. Nat. Biotechnol. 20, 901 (2002) |
| pJWS17 | Constitutive pcDNA3.1-derived pramlintide expression vector (P$_{hCMV}$-Pram-pA). Pram was excised from pUC57-Pram with XbaI/ApaI and cloned into the corresponding sites (XbaI/ApaI) of pcDNA3.1. | |
| pKR124 | Constitutive mammalian LSR expression vector (P$_{SV40}$-LSR-pA; LSR, TtgR-PPARα). PPARα was PCR-amplified from human genomic cDNA using oligonucleotides OKR189 (5'-gtacagccgcgcgcATCTCAAATCTCT GGCCAAGAG-3') and OKR190 (5'-ctatcccggatccTTAGTACATGTCCC | |

| Plasmid | Description and Cloning Strategy | Reference or Source |
|---|---|---|
| | TGTAGATC-3'), digested with BSSHII/BamHI and cloned into the corresponding sites (BSSHII/BamHI) of pMG11. | |
| pKR135 | Constitutive mammalian LSR expression vector ($P_{hCMV}$-LSR-pA). $P_{hCMV}$ was exised from pcDNA3.1 with MIuI/EcoRI and cloned into the corresponding sites (MIuI/EcoRI) of pKR124. | |
| pKR136 | Constitutive mammalian LSR expression vector ($P_{hEF1\alpha}$-LSR-PA). $P_{hEF1\alpha}$ was excised from pWW29 with SspI/KpnI and cloned into the corresponding sites (SspI/KpnI) of pKR135. | |
| pKR146 | $P_{TtgR1}$-driven pramlintide expression vector ($P_{TtgR1}$-Pram-pA). Pram was excised from pUC57-Pram with EcoRI/HindIII and cloned into the corresponding sites (EcoRI/HindIII) of pMG10. | |

Restriction endonuclease-specific sites are underlined in oligonucleotide sequences. Annealing base pairs contained in oligonucleotide sequences are shown in capital letters.

Abbreviations: CALCR, human calcitonin receptor; LSR, lipid-sensing receptor (TtgR-PPARα); MCS, multiple cloning site; MphR(A), repressor of the *Escherichia coli* 2'-phosphotransferase I; pA, SV40-derived polyadenylation site; $P_{hCMV}$, human cytomegalovirus immediate early promoter; $P_{hEF1\alpha}$, human elongation factor 1α promoter; $P_{sv40}$, simian virus 40 promoter; $P_{TtgR1}$, phloretin-responsive promoter; $P_{CRE}$, synthetic mammalian promoter containing a cAMP-response element; PPARα, human peroxisome proliferator-activated receptor alpha; Pram, pramlintide, a stabilized variant of human peptide hormone amylin; RAMP3, human calcitonin receptor-like receptor activity modifying protein 3; SEAP, human placental secreted alkaline phosphatase; $TtgA_1$, phloretin-dependent transactivator; TtgR, repressor of the *Pseudomonas putida* DOT-T1E ABC multi-drug efflux pump; VP16, Herpes simplex-derived transactivation domain.

Key plasmids include: pKR135 encodes constitutive expression of the lipid-sensing receptor (LSR; $P_{hCMV}$-LSR-PA). pMG10, harbors a SEAP expression unit driven by the LSR-specific phloretin-responsive promoter ($P_{TtgR1}$; $P_{TtgR1}$-SEAP-pA). pKR146, contains a $P_{TtgR1}$-driven pramlintide expression unit ($P_{TtgR1}$-Pram-pA).

Cell Culture, Transfection

Human embryonic kidney cells (HEK-293T, ATCC: CRL-11268), Baby hamster kidney cells (BHK-21, ATCC: CCL-10), African green monkey kidney cells (COS-7, ATCC: CRL-1651), human cervical adenocarcinoma cells (HeLa, ATCC: CCL-2), human fibrosarcoma cells (HT-1080, ATCC: CCL-121) and immortalized human mesenchymal stem cells (hMSC) (Simonsen, J. L. et al., Nat Biotechnol 20, 592-596 (2002)) were cultivated in Dulbecco's modified Eagle's medium (DMEM; Invitrogen, Basel, Switzerland) supplemented with 1% (v/v) penicillin/streptomycin solution (Sigma-Aldrich, Munich, Germany). Wild-type Chinese hamster ovary cells (CHO-K1, ATCC: CCL-61) were cultured in ChoMaster® HTS (Cell Culture Technologies GmbH, Gravesano, Switzerland) containing 1% penicillin/streptomycin. All cell types were cultivated at 37° C. in a humidified atmosphere containing 5% $CO_2$. For (co-)transfection of BHK-21, CHO-K1, COS-7, HeLa, HT-1080 and hMSCs, 40,000 cells seeded per well of a 24-well plate 12 h prior to transfection were incubated for 6 h with a 4:1 PEI:DNA mixture (Polyethyleneimine; MW 40,000, Polysciences, Inc., Warrington, USA). After transfection, all cells were cultivated in their specific media containing different inducer concentrations and reporter protein levels were profiled after 48 h unless stated otherwise.

Analytical Assays

SEAP:

Production of the human placental secreted alkaline phosphatase (SEAP) in culture was quantified according to a p-nitrophenylphosphate-based time course of light absorbance (Schlatter S. et al., Gene 282, 19-31 (2002)). Serum levels of SEAP were quantified using a chemiluminescence-based assay (Roche Diagnostics GmbH, Mannheim, Germany).

Blood Fat Levels:

Cholesterol levels in the blood were profiled using a Total Cholesterol Assay Kit-Fluoro Cholesterol (Cell Technology, Mountain View, USA), and phospholipids were quantified by a phospholipid assay kit (Abnova GmbH, Heidelberg, Germany).

Pramlintide:

In vitro activity of pramlintide was measured by (co-) transfecting HT-1080 with pKR135/pKR146 or pJWS17 (6 µg DNA, 800,000 cells, 10 cm Petri dish). 48 h after transfection, the culture medium was transferred to 60,000 HEK-293 cells that had been cotransfected with pCALCR, pRAMP3, pCK53 and pcDNA3.1 at a ratio of 1:1:0.5:7.5 (0.6 µg of total DNA) and SEAP levels were profiled after 48 h. Alternatively, pramlintide was quantified using the human amylin EIA ELISA kit (Phoenix Pharmaceuticals, Burlingame, USA) and pure pramlintide as standard (Feldan, Quebec, Canada). For quantification of pramlintide in mouse serum samples, 96-well plates were coated with 5 µg/mL (100 µL/well) rabbit polyclonal anti-human amylin (Amylin H-50, Santa Cruz Biotechnology, Santa Cruz, USA; cat. no. sc-20936, lot. no. 10303) in dilution buffer (PBS, 0.5% BSA, 0.01% Tween80, pH7.4) at 4° C. overnight. Plates were blocked with 200 µL/well PBS/1% BSA pH7.4 for 1 h at 22° C. Pramlintide standard (1 µg/mL-500 µg/mL) and samples (100 µL/well) were diluted (PBS, 0.5% BSA, 0.01% Tween80, pH 7.4) and incubated for 1.5 h at 22° C. Plates were washed three times with 250 µL/well PBS containing 0.15% Tween-20 and then incubated with 100 µL/well of a mouse monoclonal anti-Amylin (Abcam, Cambridge, UK; cat. no. ab115766, lot no. GR81110-2) for 1 h at 22° C. After three washing steps (250 µL PBS/0.15% Tween-20), the plates were incubated with an anti-mouse horseradish peroxidase-conjugated IgG (GE Healthcare, Buckinghamshire, UK, cat. no. NA931V, lot no. 399402) for 1 h at 22° C., washed again (250 µL PBS/0.15% Tween-20) and bound pramlintide was visualized by incubation of the samples with 100 µL/well of TMB substrate (Interchim, Montlugon, France) at 22° C. for 6 min. Reactions were stopped by addition of 2 M sulfuric acid (100 µL/well) and pramlintide was quantified at 450 nm using an Envision plate reader.

Animal Experiments

Intraperitoneal implants were produced by encapsulating pKR135/pMG10- or pKR135/146-transgenic HT-1080 into coherent alginate-poly-(L-lysine)-alginate beads (400 µm; 200 cells/capsule) using an Inotech Encapsulator Research Unit IE-50R (Buchi Labortechnik AG, Flawil, Switzerland) set to the following parameters: 200 µm nozzle with a vibration frequency of 1023 Hz and 900 V for bead dispersion, 20 mL syringe operated at a flow rate of 403 units. 400 µL of serum-free DMEM containing $2 \times 10^6$ microencapsulated transgenic cells (pKR135/pMG10- or pKR135/pKR146-transgenic HT-1080; 200 cells/capsule) were injected intraperitoneally into 14-week-old female CD1 (normal 5 kcal % fat diet; Janvier S. A. S., Le Genest-Saint-Isle, France) or 14-week-old diet-induced obese mice (D10, C57BL/6J, The Jackson Laboratory, Maine, USA) that were on a 10 kcal % (D12450Bi, Research Diets, Inc., N.J.) or a 60 kcal % fat diet (D12492i, Research Diets, New Brunswick, USA). CD1 mice implanted with pKR135/pMG10-transgenic HT-1080 received twice daily injections of linoleic or palmitic acid (200 µl, 0-200 mg/kg; linoleic acid, Thermo Fisher Scientific, Geel, Belgium; palmitic acid: Sigma-Aldrich) or oral doses of rapeseed oil (100 µL and 200 µL; Naturaplan Rapsöl, Coop, Basel, Switzerland). Control mice were treated with capsules containing non-engineered parental HT-1080. Every day, the food intake and body weight of the animals was profiled. After a starvation period of 4 h blood samples were collected and the serum was isolated using microtainer SST tubes according to the manufacturer's protocol (Beckton Dickinson, Plymouth, UK) before serum SEAP, blood fat and pramlintide levels were scored as described above. All experiments involving animals were performed according to the directives of the European Community Council (86/609/EEC), approved by the French Republic (no. 69266309), and carried out by Ghislaine Charpin-El Hamri at the Institut Universitaire de Technology, IUTA, F-69622 Villeurbanne Cedex, France.

The invention claimed is:

1. A vector encoding a lipid-sensing receptor comprising a nucleic acid sequence encoding the human peroxi some proliferator-activated receptor alpha (PPARα) fused to a repressor, linked to a minimal promoter to control transgene expression, wherein the PPARα fused to a repressor is a fusion protein of PPARα with TtgR that binds a TtgR-specific operator ($O_{TtgR}$) linked to the minimal promoter, and wherein the minimal promoter is the constitutive human cytomegalovirus promoter ($P_{hCMV}$).

2. A mammalian cell comprising the vector of claim 1.

3. The mammalian cell according to claim 2 in a nano-container or microcontainer.

4. The mammalian cell of claim 2, further comprising a polynucleotide coding for an endogenous or exogenous protein reducing fat intake.

5. The mammalian cell according to claim 4, wherein the endogenous or exogenous protein reducing fat intake is pramlintide.

6. The mammalian cell of claim 2, further comprising a polynucleotide coding for a detectable endogenous or exogenous protein.

7. The mammalian cell according to claim 6, wherein the detectable endogenous or exogenous protein is selected from human placental secreted alkaline phosphatase (SEAP), a fluorescent or enhanced fluorescent protein, secreted alpha amylase (SAMY), luciferase, beta-galactosidase, beta-lactamase, and glucoronidase.

8. A mammal excluding man comprising a mammalian cell according to claim 2.

* * * * *

---

SEQUENCE LISTING

<160> NUMBER OF SEQ ID NOS: 2

<210> SEQ ID NO 1
<211> LENGTH: 36
<212> TYPE: DNA
<213> ORGANISM: Artificial
<220> FEATURE:
<223> OTHER INFORMATION: Synthetic construct

<400> SEQUENCE: 1
gtacagccgc gcgcatctca aatctctggc caagag         36

<210> SEQ ID NO 2
<211> LENGTH: 35
<212> TYPE: DNA
<213> ORGANISM: Artificial
<220> FEATURE:
<223> OTHER INFORMATION: Synthetic construct

<400> SEQUENCE: 2
ctatcccgga tccttagtac atgtccctgt agatc          35